United States Patent
Fukaya et al.

(10) Patent No.: US 10,000,514 B2
(45) Date of Patent: Jun. 19, 2018

(54) METHOD FOR PRODUCING TETRAALKOXYSILANE

(71) Applicant: NATIONAL INSTITUTE OF ADVANCED INDUSTRIAL SCIENCE AND TECHNOLOGY, Tokyo (JP)

(72) Inventors: Norihisa Fukaya, Ibaraki (JP); Seong-Jib Choi, Ibaraki (JP); Jun-Chul Choi, Ibaraki (JP); Toshio Horikoshi, Ibaraki (JP); Kazuhiko Sato, Ibaraki (JP); Hiroyuki Yasuda, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days. days.

(21) Appl. No.: 15/309,900

(22) PCT Filed: Apr. 30, 2015

(86) PCT No.: PCT/JP2015/063017
§ 371 (c)(1),
(2) Date: Nov. 9, 2016

(87) PCT Pub. No.: WO2015/170666
PCT Pub. Date: Nov. 12, 2015

(65) Prior Publication Data
US 2017/0267701 A1    Sep. 21, 2017

(30) Foreign Application Priority Data
May 9, 2014   (JP) ................. 2014-097748

(51) Int. Cl.
*C07F 7/04* (2006.01)
(52) U.S. Cl.
CPC ................... *C07F 7/045* (2013.01)
(58) Field of Classification Search
CPC ...................................... C07F 7/045
USPC ........................................ 556/470
See application file for complete search history.

(56) References Cited

U.S. PATENT DOCUMENTS

| 2,473,260 | A |   | 6/1949 | Rochow |   |
|---|---|---|---|---|---|
| 2,881,198 | A |   | 4/1959 | Bailey et al. |   |
| 4,730,074 | A |   | 3/1988 | Lewis et al. |   |
| 6,288,257 | B1 | * | 9/2001 | Schattenmann | ........ C07F 7/045 423/325 |

FOREIGN PATENT DOCUMENTS

| JP | 62-114991 |   | 5/1987 |
|---|---|---|---|
| JP | 04-338393 |   | 11/1992 |
| JP | 3026371 |   | 1/2000 |
| JP | 2000-178283 |   | 6/2000 |
| JP | 2001-114786 |   | 4/2001 |
| JP | 2006-083065 |   | 3/2006 |
| JP | 2006-188443 |   | 7/2006 |
| JP | 2008-024593 |   | 7/2008 |
| JP | 2009-242306 |   | 10/2009 |
| JP | 2009242306 | A * | 10/2009 |
| JP | 2014-051455 |   | 3/2014 |

OTHER PUBLICATIONS

Lewis et al., Inorg Chem. 41(9), 2002, 2608-2615.*
Search Report in International Application No. PCT/JP2015/063017 dated Aug. 4, 2015, 4 pages.
International Preliminary Report on Patentability and Written Opinion in International Application No. PCT/JP2015/063017 dated Nov. 24, 2016, 6 pages.
Extended European Search Report in EP Application No. 15789345.4 dated Nov. 23, 2017, 7 pages.
Office Action for Chinese Application No. 201580024399.X, dated Mar. 28, 2018.

* cited by examiner

*Primary Examiner* — Rosalynd Keys
*Assistant Examiner* — Kofi Adzamli
(74) *Attorney, Agent, or Firm* — Marshall, Gerstein & Borun LLP

(57) ABSTRACT

An object of the present invention is to provide a method for producing tetraalkoxysilane while saving energy at a high yield. Tetraalkoxysilane can be produced while saving energy at a high yield by the method including a first step of reacting alcohol with carbon dioxide in the presence of a dehydrating agent and/or in a reactor provided with a dehydrating means, and a second step of reacting a reaction mixture obtained in the first step with silicon oxide.

7 Claims, 1 Drawing Sheet

METHOD FOR PRODUCING TETRAALKOXYSILANE

TECHNICAL FIELD

The present invention relates to a highly efficient method for producing tetraalkoxysilane, and more specifically relates to a method for producing tetraalkoxysilane by utilizing carbon dioxide.

BACKGROUND ART

Tetraalkoxysilane is used as a raw material for manufacturing various silane compounds, organic silicone polymers, various silylating agents, colloidal silicas, and ceramics.

A common method for producing industrially alkoxysilanes is a method in which natural silicon dioxide as a starting raw material is mixed with carbon and then reduced at high temperature to yield metal silicon, which is then made to react with chlorine to produce tetrachlorosilane, followed by a further reaction with alcohol (See PATENT DOCUMENT 1.). Other methods are also known in which metal silicon is reacted directly with alcohol (See PATENT DOCUMENTS 2 and 3.).

All of these methods, however, must undergo a process of producing metal silicon which requires high temperature, and therefore, they are problematic owing to the poor energy efficiency.

On the other hand, methods of producing alkoxysilane directly from silica are known wherein silica is reacted with an alkyl carbonate with the aid of an alkali metal element or an alkaline earth metal element as a catalyst, to produce alkoxysilane (See PATENT DOCUMENTs 4 and 5.). While these methods do not use metal silicon as a raw material, and therefore, are advantageous in energy efficiency, they require an alkyl carbonate, a relatively expensive compound, fed in a molar quantity stoichiometrically at least twice as much as silica, and therefore, are problematic as an industrial method for producing tetraalkoxysilane.

PRIOR ART REFERENCES

Patent Documents

[PATENT DOCUMENT 1] JP-A-62-114991
[PATENT DOCUMENT 2] US Patent Application No. 2473260
[PATENT DOCUMENT 3] JP A 2000 430009 JP-A-2000-178283
[PATENT DOCUMENT 4] JP-A-2001-114786
[PATENT DOCUMENT 5] Japanese Patent Application No. 3026371

DISCLOSURE OF THE INVENTION

Problem to be Solved

An object of the present invention is to provide a method for producing tetraalkoxysilane while saving energy at a high yield.

Means for Solving the Problem

The present inventors carried out an intensive investigation to solve the above object and have found that tetraalkoxysilane was able to be produced while saving energy at a high yield by reacting alcohol with carbon dioxide and then making the reaction mixture thereof react with silicon oxide and by using a dehydration agent to remove appropriately water generated in the reaction, and thereby the inventors have accomplished the invention.

Thus, the present invention is as follows.

<1> A method for producing tetraalkoxysilane by using alcohol and silicon oxide, comprising:
a first step of reacting alcohol with carbon dioxide in the presence of a dehydrating agent and/or in a reactor provided with a dehydrating means; and
a second step of reacting a reaction mixture obtained in the first step with silicon oxide.

<2> The method for producing tetraalkoxysilane according to <1>, wherein the first step is performed in the presence of at least one metal compound selected from the group consisting of a metal alkoxide, an organic metal oxide, and an inorganic metal oxide.

<3> The method for producing tetraalkoxysilane according to <2>, wherein a metal element of the metal compound is titanium, tin, or zirconium.

<4> The method for producing tetraalkoxysilane according to any one of <1> to <3>, wherein the dehydrating agent(s) is (are) an organic dehydrating agent and/or an inorganic dehydrating agent.

<5> The method for producing tetraalkoxysilane according to <4>, wherein the organic dehydrating agent is an acetal represented by the following general formula (1),

wherein $R^1$ and $R^2$ independently represent a hydrogen atom or a hydrocarbon group of 1 to 15 carbons, and R represents a hydrocarbon group of 1 to 15 carbons, with the proviso that both of $R^1$ and $R^2$ are not a hydrogen atom simultaneously.

<6> The method for producing tetraalkoxysilane according to any one of <1> to <5>, wherein the second step is performed in the presence of an alkali metal compound and/or an alkaline earth metal compound.

<7> The method for producing tetraalkoxysilane according to <6>, wherein the alkali metal compound is at least one selected from the group consisting of an alkali metal hydroxide, an alkali metal halide, an alkali metal carbonate, and an alkali metal hydrogen carbonate.

<8> The method for producing tetraalkoxysilane according to any one of <1> to <7>, wherein the alcohol, the silicon oxide, and the carbon dioxide coexist in one reaction system, and thereby the first step and the second step proceed in the one reaction system.

Effect of the Invention

According to the present invention, tetraalkoxysilane can be provided at a high yield by utilizing silicon oxide without going through the route of metal silicon. Accordingly, the present invention is superior to conventional methods in energy efficiency and enables producing tetraalkoxysilane at low costs.

EMBODIMENTS FOR CARRYING OUT THE INVENTION

Figure 1:
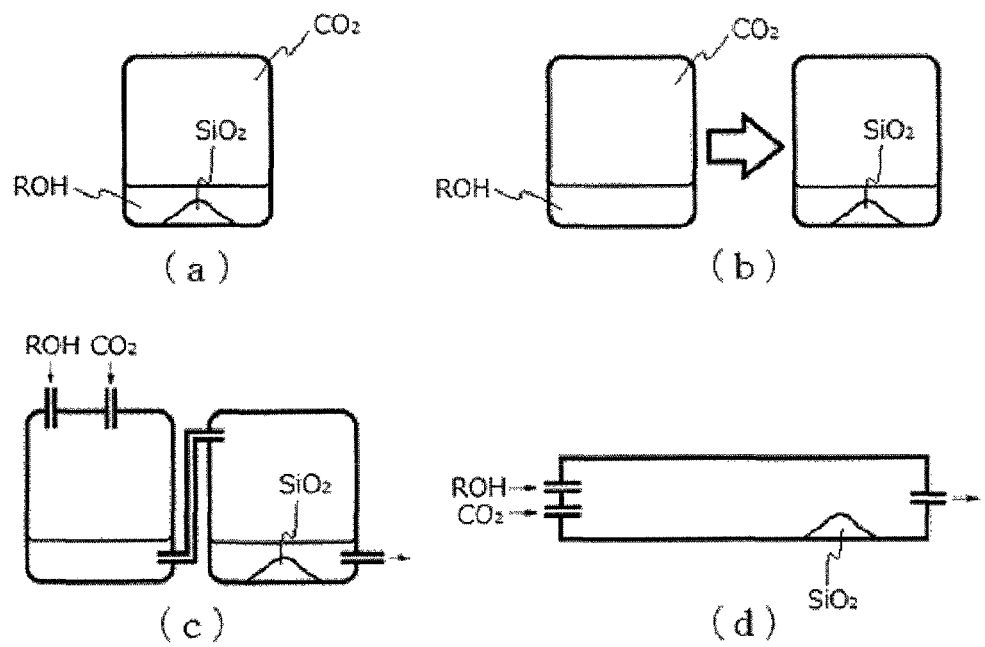
FIG. 1 is a conceptual drawing of a reactor which can be used for a method for producing tetraalkoxysilane which is an embodiment of the present invention ((a), (b) batch reactors; (c) continuous stirred tank reactor; (d) plug flow reactor).

Although the present invention will be described with reference to specific examples, it is not limited to the following contents and can be modified for its implementation so long as it does not depart from the gist of the invention.

<Method for Producing Tetraalkoxysilane>

A method for producing tetraalkoxysilane which is one embodiment of the present invention (hereinafter it may be referred to as production method of the invention) is a method for producing tetraalkoxysilane by using alcohol and silicon oxide and comprises a first step and a second step described below.

The first step: a process in which the alcohol is reacted with carbon dioxide in the presence of a dehydrating agent and/or in a reactor provided with a dehydrating means.

The second step: a process in which a reaction mixture obtained in the first step is reacted with the silicon oxide.

The present inventors focused a method using alcohol and silicon oxide as a method for producing tetraalkoxysilane without going through the route of metal silicon and carried out its study; as a result, they have eventually found that tetraalkoxysilane can be produced efficiently by the coexistence of carbon dioxide during the reaction of the alcohol with the silicon oxide. This is attributed to the activated alcohol owing to the reaction with the carbon dioxide, which subsequently leads to the more efficient reaction with the silicon oxide. In other words, carbon dioxide is considered to act as a reaction accelerator. This method can minimize unnecessary waste materials by recovering and reusing carbon dioxide, and moreover, utilizes alcohol and silicon oxide which are inexpensive and common materials as starting raw materials; therefore, this method can be said to be an industrially highly suitable method.

Further the inventors have also confirmed that the yield of tetraalkoxysilane is significantly worsened if water generated owing to the reaction is not removed by utilizing a dehydrating agent among others.

As a consequence, the production method of the present invention comprising the first step and the second step is a method which enables producing tetraalkoxysilane while saving energy at a high yield.

The expression of "comprises a first step and a second step" means that the method is not limited to an embodiment in which the steps proceed independently, and that it may be a method in which, for example, alcohol, silicon oxide, and carbon dioxide coexist in one reaction system, and thereby the first step and the second step proceed in the one reaction system. Accordingly, the production method of the invention includes any one of: the embodiment as shown in (a) of FIG. 1, which feeds alcohol, silicon oxide, and carbon dioxide into a batch reactor for the first step and the second step to proceed; the embodiment as shown in (b) of FIG. 1, which makes alcohol react with carbon dioxide in a batch reactor, followed by feeding silicon oxide to make it react with the reaction mixture; the embodiment as shown in (c) of FIG. 1, which sequentially feeds, into a continuous stirred tank reactor, alcohol and carbon dioxide, a reaction mixture of which is then moved into another continuous stirred tank reactor, to make the mixture react with silicon oxide, followed by recovering tetraalkoxysilane sequentially; and the embodiment as shown in (d) of FIG. 1, which feeds sequentially alcohol and carbon dioxide into a plug flow reactor to make them react with silicon oxide, followed by recovering tetraalkoxysilane sequentially.

(First Step)

The first step is a step of reacting alcohol with carbon dioxide in the presence of a dehydrating agent and/or in a reactor provided with a dehydrating means, and the kind of the alcohol is not especially limited and can be suitably selected depending on tetraalkoxysilane which is a production target. For example, when methanol is used as the alcohol, tetramethoxysilane can be produced, and when ethanol is used, tetraethoxysilane can be produced.

The alcohol may be an aliphatic alcohol or an aromatic alcohol, and a hydrocarbon group in the alcohol may have any one of structures including a branching structure, a ring-shaped structure, and an unsaturated carbon-carbon bond.

The number of carbons in the alcohol is usually one or more, preferably 15 or less, more preferably 10 or less, and still more preferably 8 or less.

Specific examples of the alcohol include methanol, ethanol, 1-propanol, 2-propanol, 1-butanol, 2-butanol, 2-methyl-1-propanol, 2-methyl-2-propanol, benzyl alcohol, and phenol. Among them, methanol and ethanol are preferable, and methanol is more preferable.

The first step is carried out preferably in the presence of at least one metal compound selected from the group consisting of a metal alkoxide, an organic metal oxide, and an inorganic metal oxide. The existence of these metal compounds makes the alcohol more reactive with carbon dioxide, and as a result, tetraalkoxysilane can be produced at a high yield. The alkoxy group of the metal alkoxide preferably has the same hydrocarbon group as that of the alcohol which is reacted with carbon dioxide.

The metal element of the metal compound is preferably at least one selected from the group consisting of titanium, tin, and zirconium.

Specific examples of the metal alkoxide include tetramethoxy titanium, tetraethoxy titanium, tetraisopropoxy titanium, tetrabutoxy titanium, tetramethoxy zirconium, tetraethoxy zirconium, tetramethoxy tin, tetraethoxy tin, tetra-t-butoxy tin, di-n-butyl dimethoxy tin, di-n-butyl diethoxy tin, and di-n-butyl dibutoxy tin.

Specific examples of the organic metal oxide include dimethyl tin oxide, diethyl tin oxide, diisopropyl tin oxide, and di-n-butyl tin oxide.

Specific examples of the inorganic metal oxide include zirconium oxide, tin oxide, and titanium oxide.

The metal compound may be used singly or in combination of two or more kinds thereof.

The amount of the metal compound to be used is usually 0 mmol or more, preferably 0.01 mmol or more, and more preferably 0.1 mmol or more, and usually 1 mol or less, preferably 500 mmol or less, and more preferably 100 mmol or less, with respect to 1 mol of alcohol.

In the first step, a reactor, an operation procedure, and a reaction condition for the reaction of alcohol with carbon dioxide in the presence of a dehydrating agent and/or in the reactor provided with a dehydrating means are not especially limited and can be appropriately selected depending on a purpose.

Examples of the reactor include a batch reactor (See (a), (b) of FIG. 1.), a continuous stirred tank reactor (See (c) of FIG. 1.), a plug flow reactor (See (d) of FIG. 1.), and so on, as described above. The batch reactor is preferably a pressure resistant reactor such as an autoclave.

When, for example, a batch reactor is used, examples of the operation procedure include a method of feeding alcohol, a dehydrating agent, a metal compound, and so on into the reactor, and then scavenging the inside of the reaction vessel with carbon dioxide gas, followed by charging with carbon dioxide and sealing the reactor, which is then heated up to a reaction temperature. The charging pressure at 25° C. of carbon dioxide is preferably within the range from 0.1 to 10 MPa. The above range enables producing tetraalkoxysilane at a high yield.

Further, when a continuous stirred tank reactor or a plug flow reactor is used, examples of the procedure include a method of feeding alcohol, a dehydrating agent, carbon dioxide, a metal compound, and so on, in the form of vapor or liquid, each continuously into the reactor heated up to a reaction temperature. A carrier gas may be used to feed the alcohol, the dehydrating agent, the carbon dioxide, the metal compound, and so on. Examples of the carrier gas to be used include an inert gas such as nitrogen and argon gases, and carbon dioxide gas itself. The feeding rate of the gas such as the carrier gas and carbon dioxide can be appropriately selected depending on the size of the reactor and the reaction condition.

The reaction temperature in the first step is usually 50° C. or more, preferably 80° C. or more, and more preferably 100° C. or more, and usually 500° C. or less, preferably 400° C. or less, and more preferably 300° C. or less.

The reaction pressure in the first step is usually 0.1 MPa or more, preferably 1.0 MPa or more, and more preferably 3.0 MPa or more, and usually 60 MPa or less, preferably 30 MPa or less, and more preferably 20 MPa or less. The partial pressure of the carbon dioxide is usually 0 MPa or more, preferably 0.1 MPa or more, and more preferably 0.2 MPa or more, and usually 50 MPa or less, preferably 20 MPa or less, and more preferably 10 MPa or less.

The reaction time in the first step is usually 1 hour or more, preferably 5 hours or more, and more preferably 10 hours or more, and usually 168 hours or less, preferably 120 hours or less, and more preferably 100 hours or less.

The above ranges enable producing tetraalkoxysilane at a high yield.

The dehydrating agent in the first step means an agent which reacts with water chemically or adsorbs water physically to remove the water, and any known dehydrating agent may be appropriately selected without any especial limitation to a specific kind thereof.

Specific examples of the dehydrating agent include an organic dehydrating agent such as an acetal and an acid anhydride, an inorganic dehydrating agent, such as magnesium sulfate, sodium sulfate, calcium chloride, calcium oxide, phosphorous (V) oxide, and aluminum oxide, and an adsorption agent such as a molecular sieve. Among them, from the viewpoint of their ability of uniform action in the reaction system, organic dehydrating agents are preferable and acetals represented by the following general formula (1),

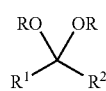
(1)

are more preferable, wherein $R^1$ and $R^2$ independently represent a hydrogen atom or a hydrocarbon group of 1 to 15 carbons, and R represents a hydrocarbon group of 1 to 15 carbons, with the proviso that both of $R^1$ and $R^2$ are not a hydrogen atom simultaneously.

The alkoxy group of the acetal preferably has the same hydrocarbon group as that of the alcohol which is reacted with the carbon dioxide. When the dehydrating agent is an acetal, the agent reacts with water, as shown in the following reaction formula (2), to produce the alcohol, which can be utilized for the reaction with the carbon dioxide. In addition, after the completion of the reaction, recovered aldehyde and ketone can be easily retransformed into the acetal to be reused.

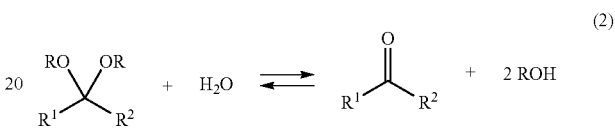
(2)

Specific examples of the acetal represented by the general formula (1) include benzaldehyde dimethyl acetal, acetaldehyde dimethyl acetal, formaldehyde dimethyl acetal, acetone dimethyl acetal (2,2-dimethoxypropane), acetone diethyl acetal, acetone dibenzyl acetal, diethyl ketone dimethyl acetal, benzophenone dimethyl acetal, benzyl phenyl ketone dimethyl acetal, cyclohexanone dimethyl acetal, acetophenone dimethyl acetal, 2,2-dimethoxy-2-phenyl acetophenone, 4,4-dimethoxy-2,5-cyclohexadiene-1-one acetal, and dimethyl acetamide diethyl acetal. The acetal may be used singly or in combination of two or more kinds thereof.

The amount of the acetal to be used is usually 0 mol or more, preferably 0.001 mol or more, and more preferably 0.005 mol or more, and usually 1 mol or less, preferably 0.8 mol or less, and more preferably 0.5 mol or less, with respect to 1 mol of alcohol. The above range enables producing tetraalkoxysilane at a high yield.

The reactor provided with a dehydrating means in the first step means that the reactor is provided with a material or a device which can separate water, and any known reactor may be appropriately selected without any especial limitation to a specific separation means.

Figure 2:
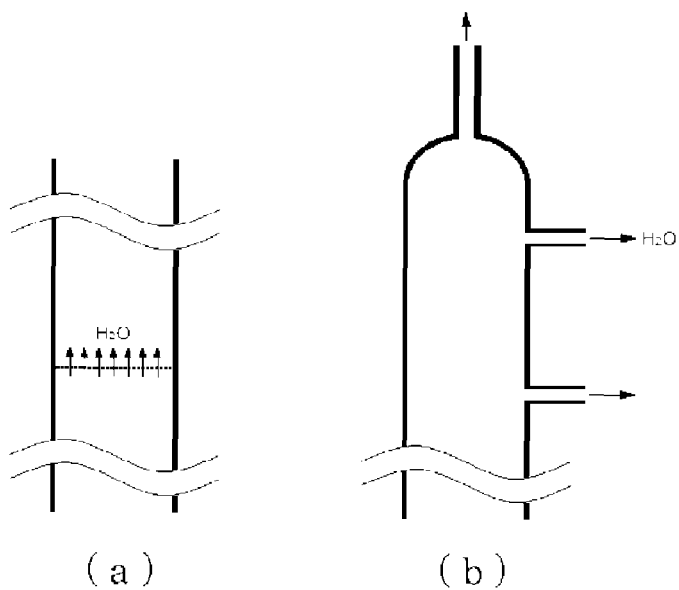
FIG. 2 is a conceptual drawing of a dehydrating means disposed in a reactor used in the first step ((a) separation film; (b) distillation apparatus).

Specific examples of the dehydrating means include a separation film as shown in (a) of FIG. 2 and a distillation device shown in (b) of FIG. 2. Specific examples of the separation film include a carbon film, a silica film, a zeolite film, and a polymer film.

(Second Step)

The second step is a step of reacting a reaction mixture obtained in the first step with silicon oxide, which means a compound containing a silicon atom (Si) and an oxygen atom (O) as main elements and means that it may be a composite oxide of a compound such as silicon monoxide (SiO), silicon dioxide (SiO2), and zeolite, with another metal.

Specific examples of the silicon oxide include a natural mineral, such as silica, silica sand, diatomite, quartz, fired ash of a silicon-containing plant, volcanic ash, silicates, silicagel originated from silica sol, fumed silica, silica alumina, and zeolite.

The second step is carried out preferably in the presence of an alkali metal compound and/or an alkaline earth metal compound. The existence of the alkali metal compound and the alkaline earth metal compound enhances the cleavage of a silicon-oxygen bond of the silicon oxide, and consequently, tetraalkoxysilane can be produced at a high yield.

Examples of the alkali metal and the alkaline earth metal in the alkali metal compound and the alkaline earth metal compound include lithium (Li), sodium (Na), magnesium (Mg), potassium (K), calcium (Ca), cesium (Cs), and so on. Further, examples of the counter ion in the compounds include a hydroxide, a halide, an oxide, a carbonate, a hydrogen carbonate, an alkoxide, a silicate, an aluminate, a phosphonate, a salt of organic acid, a sulfate, a nitrate, and so on. Among them, the hydroxide, the halide, the carbonate, and the hydrogen carbonate are preferable, and an alkali metal hydroxide, an alkali metal halide, an alkali metal carbonate, and an alkali metal hydrogen carbonate are more preferable.

Specific examples of the alkali metal compound and the alkaline earth metal compound include lithium hydroxide, sodium hydroxide, potassium hydroxide, calcium hydroxide, cesium hydroxide, lithium carbonate, sodium carbonate, potassium carbonate, cesium carbonate, sodium fluoride, potassium fluoride, and cesium fluoride. The alkali metal compound and the alkaline earth metal compound may be used singly or in combination of two or more kinds thereof.

The total amount of the alkali metal compound and the alkaline earth metal compound to be used is usually 0 mol or more and preferably 0.001 mol or more, and usually 20 mol or less and preferably 10 mol or less, with respect to 1 mol of silicon oxide (in the case of silicon dioxide).

In the second step, a reactor, an operation procedure, and a reaction condition for the reaction of a reaction mixture obtained in the first step with silicon oxide are not especially limited and can be appropriately selected depending on a purpose.

Examples of the reactor include a batch reactor (See (a), (b) of FIG. 1.), a continuous stirred tank reactor (See (c) of FIG. 1.), and a plug flow reactor (See (d) of FIG. 1.), as in the case of the first step. The batch reactor is preferably a pressure resistant reactor such as an autoclave.

When, for example, a batch reactor is used, examples of the operation procedure include a method of feeding the reaction mixture obtained in the first step, silicon oxide, and an alkali metal compound, and so on into the reactor, and then scavenging the inside of the reaction vessel with an inert gas, followed by charging with the inert gas and sealing the reactor, which is then heated up to a reaction temperature.

Further, when a continuous stirred tank reactor or a plug flow reactor is used, examples of the procedure include a method of feeding, in advance, silicon oxide, an alkali metal compound, and so on into the reactor, and then heating the reaction vessel up to a reaction temperature, followed by feeding a reaction mixture obtained in the first step, in the form of vapor or liquid, continuously into the reaction vessel. A carrier gas may be used to feed the reaction mixture obtained in the first step.

The reaction temperature in the second step is usually 50° C. or more, preferably 80° C. or more, and more preferably 100° C. or more, and usually 500° C. or less, preferably 400° C. or less, and more preferably 300° C. or less.

The reaction pressure in the second step is usually 0.1 MPa or more, preferably 1.0 MPa or more, and more preferably 3.0 MPa or more, and usually 60 MPa or less, preferably 30 MPa or less, and more preferably 20 MPa or less. The partial pressure of carbon dioxide is usually 0 MPa or more, preferably 0.1 MPa or more, and more preferably 0.2 MPa or more, and usually 50 MPa or less, preferably 20 MPa or less, and more preferably 10 MPa or less.

The reaction time in the second step is usually 1 hour or more, preferably 5 hours or more, and more preferably 10 hours or more, and usually 168 hours or less, preferably 120 hours or less, and more preferably 100 hours or less.

The above ranges enable producing tetraalkoxysilane at a high yield.

Although the production method of the present invention comprises the first step and the second step, it is not limited to a method in which each of the reactions in the first and second steps independently proceeds as described above, and it may be a method in which, for example, alcohol, silicon oxide, and carbon dioxide coexist in one reaction system, and thereby the first and second steps proceed in the one reaction system. Such an embodiment can be, in other words, represented as the following method.

A method for producing tetraalkoxysilane, including a reaction step of reacting alcohol with silicon oxide, wherein the reaction step is a step satisfying the following conditions (a) and (b) of:

(a) performing the reaction in the presence of carbon dioxide; and (b) performing the reaction in the presence of a dehydrating agent and/or in a reactor provided with a dehydrating means.

Also in an embodiment in which the first and second steps proceed in one reaction system, the steps are carried out preferably in the presence of at least one metal compound selected from the group consisting of a metal alkoxide, an organic metal oxide, and an inorganic metal oxide. The detail of the metal compound was described above.

Further, also in the embodiment in which the first and second steps proceed in the one reaction system, the steps are preferably carried out in the presence of alkali metal compound and/or an alkaline earth metal compound. The detail of the alkali metal compound and/or the alkaline earth metal compound was described above.

A reactor, an operating procedure, and a reaction condition for carrying out the first and second steps in one reaction system are not especially limited and can be appropriately selected depending on a purpose.

Examples of the reactor include a batch reactor (See (a) of FIG. 1.) and a plug flow reactor (See (d) of FIG. 1.), as described above. The batch reactor is preferably a pressure resistant reactor such as an autoclave.

When, for example, a batch reactor is used, examples of the operation procedure include a method of feeding alcohol, silicon oxide, a dehydrating agent, a metal compound, an alkali metal compound, and so on into a reactor, then scavenging the inside of the reaction vessel with carbon dioxide gas, followed by charging with carbon dioxide and sealing the reactor, which is then heated up to a reaction temperature. The charging pressure at 25° C. of carbon dioxide is preferably within the range from 0.1 to 10 MPa. The above range enables producing tetraalkoxysilane at a high yield.

Further, when a plug flow reactor is used, examples of the procedure include a method of feeding, in advance, silicon oxide, a dehydrating agent, an alkali metal compound, and so on into the reactor, and then heating the reaction vessel up to a reaction temperature, followed by feeding alcohol, carbon dioxide, a metal compound, and so on, in the form of vapor or liquid, each continuously into the reaction vessel. A carrier gas may be used to feed the alcohol, the carbon dioxide, the metal compound, and so on. Examples of the carrier gas to be used include an inert gas such as nitrogen and argon gases, and carbon dioxide gas itself. The feeding rate of the gas such as the carrier gas and carbon dioxide can be appropriately selected depending on the size of the reactor and the reaction condition.

The reaction temperature is usually 50° C. or more, preferably 80° C. or more, and more preferably 100° C. or more, and usually 500° C. or less, preferably 400° C. or less, and more preferably 300° C. or less.

The reaction pressure is usually 0.1 MPa or more, preferably 1.0 MPa or more, more preferably 3.0 MPa or more, and usually 60 MPa or less, preferably 30 MPa or less, and more preferably 20 MPa or less. The partial pressure of the carbon dioxide is usually 0 MPa or more, preferably 0.1 MPa or more, and more preferably 0.2 MPa or more, and usually 50 MPa or less, preferably 20 MPa or less, and more preferably 10 MPa or less.

The reaction time is usually 1 hour or more, preferably 5 hours or more, and more preferably 10 hours or more, and usually 168 hours or less, preferably 120 hours or less, and more preferably 100 hours or less.

The above ranges enable producing tetraalkoxysilane at a high yield.

EXAMPLES

Although the present invention will be described more concretely with reference to Examples and Comparative Examples, it can be appropriately modified so long as it does not depart from the gist of the present invention.

Accordingly, the scope of the present invention should not be construed exclusively to the following specific examples.

Example 1

0.18 g of Silicon dioxide (FUJI SILYSIA CHEMICAL LTD., CARiACT Q-10), 3.0 g of methanol, 5.0 g of acetone dimethyl acetal (2,2-dimethoxypropane) as an organic dehydrating agent, and 0.02 g of potassium hydroxide were added to a stainless autoclave of 20 mL volume (from Nitto Koatsu Co., Ltd.) containing a magnetic stirrer, and then the autoclave was charged with carbon dioxide from a cylinder at a temperature of 25° C. so as to keep its internal pressure at 2 MPa indicated by a pressure gauge (Swagelok FST, Inc., PGI-50M-MG10), and left for 10 minutes while stirring and then sealed. Then, the autoclave was heated up to 242° C. while being stirred at 1200 rpm, so that the reaction proceeded for 24 hours. After the autoclave was cooled, remaining carbon dioxide was evacuated therefrom, and then the reaction mixture was analyzed by gas chromatography (SHIMADZU CORPORATION, GC-2014ATF/SPL). Tetramethoxysilane was obtained at the yield of 47% based on silicon dioxide. The result is shown in Table 1-1.

Example 2

Tetramethoxysilane was produced by the same operation as that in Example 1 concerning the reaction condition therein with the exception that the reaction time was set to be 96 hours. Tetramethoxysilane was obtained at the yield of 88% based on silicon dioxide. The result is shown in Table 1-1.

Example 3

Tetramethoxysilane was produced by the same operation as that in Example 1 concerning the reaction condition therein with the exception that the pressure of carbon dioxide was set to be 0.8 MPa. Tetramethoxysilane was obtained at the yield of 27% based on silicon dioxide. The result is shown in Table 1-1.

Example 4

Tetramethoxysilane was produced by the same operation as that in Example 1 concerning the reaction condition therein with the exception that the pressure of carbon dioxide was set to be 1.2 MPa. Tetramethoxysilane was obtained at the yield of 40% based on silicon dioxide. The result is shown in Table 1-1.

Example 5

Tetramethoxysilane was produced by the same operation as that in Example 1 concerning the reaction condition therein with the exception that the pressure of carbon dioxide was set to be 0.4 MPa. Tetramethoxysilane was obtained at the yield of 7% based on silicon dioxide. The result is shown in Table 1-1.

Example 6

Tetramethoxysilane was produced by the same operation as that in Example 1 concerning the reaction condition therein with the exception that the pressure of carbon dioxide was set to be 3.0 MPa. Tetramethoxysilane was obtained at the yield of 46% based on silicon dioxide. The result is shown in Table 1-1.

Example 7

Tetramethoxysilane was produced by the same operation as that in Example 1 concerning the reaction condition therein with the exception that the pressure of carbon dioxide was set to be 4.8 MPa. Tetramethoxysilane was obtained at the yield of 30% based on silicon dioxide. The result is shown in Table 1-1.

Example 8

Tetramethoxysilane was produced by the same operation as that in Example 1 concerning the reaction condition therein with the exception that potassium hydroxide was replaced with sodium hydroxide (0.013 g). Tetramethoxysilane was obtained at the yield of 32% based on silicon dioxide. The result is shown in Table 1-1.

Example 9

Tetramethoxysilane was produced by the same operation as that in Example 1 concerning the reaction condition therein with the exception that potassium hydroxide was replaced with cesium hydroxide (0.045 g). Tetramethoxysilane was obtained at the yield of 52% based on silicon dioxide. The result is shown in Table 1-1.

Example 10

Tetramethoxysilane was produced by the same operation as that in Example 1 concerning the reaction condition therein with the exception that potassium hydroxide was replaced with lithium hydroxide (0.012 g). Tetramethoxysilane was obtained at the yield of 8% based on silicon dioxide. The result is shown in Table 1-1.

Example 11

Tetramethoxysilane was produced by the same operation as that in Example 1 concerning the reaction condition therein with the exception that potassium hydroxide was replaced with lithium carbonate (0.022 g). Tetramethoxysilane was obtained at the yield of 10% based on silicon dioxide. The result is shown in Table 1-1.

Example 12

Tetramethoxysilane was produced by the same operation as that in Example 2 concerning the reaction condition therein with the exception that potassium hydroxide was replaced with sodium carbonate (0.029 g). Tetramethoxysilane was obtained at the yield of 30% based on silicon dioxide. The result is shown in Table 1-1.

Example 13

Tetramethoxysilane was produced by the same operation as that in Example 1 concerning the reaction condition therein with the exception that potassium hydroxide was replaced with potassium carbonate (0.036 g). Tetramethoxysilane was obtained at the yield of 56% based on silicon dioxide. The result is shown in Table 1-1.

Example 14

Tetramethoxysilane was produced by the same operation as that in Example 1 concerning the reaction condition therein with the exception that potassium hydroxide was replaced with cesium carbonate (0.069 g). Tetramethoxysilane was obtained at the yield of 60% based on silicon dioxide. The result is shown in Table 1-1.

Example 15

Tetramethoxysilane was produced by the same operation as that in Example 1 concerning the reaction condition therein with the exception that potassium hydroxide was replaced with sodium fluoride (0.013 g). Tetramethoxysilane was obtained at the yield of 17% based on silicon dioxide. The result is shown in Table 1-1.

Example 16

Tetramethoxysilane was produced by the same operation as that in Example 1 concerning the reaction condition therein with the exception that potassium hydroxide was replaced with potassium fluoride (0.018 g). Tetramethoxysilane was obtained at the yield of 50% based on silicon dioxide. The result is shown in Table 1-2.

Example 17

Tetramethoxysilane was produced by the same operation as that in Example 1 concerning the reaction condition therein with the exception that potassium hydroxide was replaced with cesium fluoride (0.04 g). Tetramethoxysilane was obtained at the yield of 53% based on silicon dioxide. The result is shown in Table 1-2.

Example 18

Tetramethoxysilane was produced by the same operation as that in Example 3 concerning the reaction condition therein with the exception that 1.0 mol % of tetramethoxy titanium (with respect to 1 mol of alcohol) was added. Tetramethoxysilane was obtained at the yield of 51% based on silicon dioxide. The result is shown in Table 1-2.

Example 19

Tetramethoxysilane was produced by the same operation as that in Example 3 concerning the reaction condition therein with the exception that 1.5 mol % of tetramethoxy titanium (with respect to 1 mol of alcohol) was added. Tetramethoxysilane was obtained at the yield of 43% based on silicon dioxide. The result is shown in Table 1-2.

Example 20

Tetramethoxysilane was produced by the same operation as that in Example 3 concerning the reaction condition therein with the exception that 0.1 mol % of tetramethoxy titanium (with respect to 1 mol of alcohol) was added. Tetramethoxysilane was obtained at the yield of 33% based on silicon dioxide. The result is shown in Table 1-2.

Example 21

Tetramethoxysilane was produced by the same operation as that in Example 3 concerning the reaction condition therein with the exception that 0.01 mol % of tetramethoxy titanium (with respect to 1 mol of alcohol) was added. Tetramethoxysilane was obtained at the yield of 37% based on silicon dioxide. The result is shown in Table 1-2.

Example 22

Tetramethoxysilane was produced by the same operation as that in Example 5 concerning the reaction condition therein with the exception that 0.1 mol % of tetramethoxy titanium (with respect to 1 mol of alcohol) was added. Tetramethoxysilane was obtained at the yield of 18% based on silicon dioxide. The result is shown in Table 1-2.

Example 23

Tetramethoxysilane was produced by the same operation as that in Example 1 concerning the reaction condition therein with the exception that 0.1 mol % of tetramethoxy titanium (with respect to 1 mol of alcohol) was added. Tetramethoxysilane was obtained at the yield of 48% based on silicon dioxide. The result is shown in Table 1-2.

Example 24

Tetramethoxysilane was produced by the same operation as that in Example 1 concerning the reaction condition therein with the exception that 0.1 mol % of tetraethoxy zirconium (with respect to 1 mol of alcohol) was added. Tetramethoxysilane was obtained at the yield of 23% based on silicon dioxide. The result is shown in Table 1-2.

Example 25

Tetramethoxysilane was produced by the same operation as that in Example 1 concerning the reaction condition therein with the exception that 0.1 mol % of tetra-t-butoxy tin (with respect to 1 mol of alcohol) was added. Tetramethoxysilane was obtained at the yield of 29% based on silicon dioxide. The result is shown in Table 1-2.

Example 26

Tetramethoxysilane was produced by the same operation as that in Example 1 concerning the reaction condition therein with the exception that 0.1 mol % of pentaethoxy niobium (with respect to 1 mol of alcohol) was added. Tetramethoxysilane was obtained at the yield of 66% based on silicon dioxide. The result is shown in Table 1-2.

Example 27

Tetramethoxysilane was produced by the same operation as that in Example 3 concerning the reaction condition therein with the exception that 0.1 mol % of di-n-butyldimethoxy tin (with respect to 1 mol of alcohol) was added. Tetramethoxysilane was obtained at the yield of 6% based on silicon dioxide. The result is shown in Table 1-2.

Example 28

Tetramethoxysilane was produced by the same operation as that in Example 1 concerning the reaction condition therein with the exception that the reaction temperature was set to be 200° C. Tetramethoxysilane was obtained at the yield of 17% based on silicon dioxide. The result is shown in Table 1-2.

Example 29

Tetramethoxysilane was produced by the same operation as that in Example 1 concerning the reaction condition therein with the exception that the reaction temperature was set to be 180° C. Tetramethoxysilane was obtained at the yield of 6% based on silicon dioxide. The result is shown in Table 1-2.

Example 30

Tetramethoxysilane was produced by the same operation as that in Example 1 concerning the reaction condition therein with the exception that 0.18 g of AEROSIL 200 (from NIPPON AEROSIL CO., LTD.) was used as silicon dioxide. Tetramethoxysilane was obtained at the yield of 48% based on silicon dioxide. The result is shown in Table 1-2.

Comparative Example 1

Tetramethoxysilane was produced by the same operation as that in Example 1 concerning the reaction condition therein with the exception that neither potassium hydroxide nor 2,2-dimethoxypropane was added. Tetramethoxysilane was obtained at the yield of 1% or less based on silicon dioxide. The result is shown in Table 1-3.

Comparative Example 2

Tetramethoxysilane was produced by the same operation as that in Example 1 concerning the reaction condition therein with the exception that neither carbon dioxide was introduced, nor 2,2-dimethoxypropane was added. Tetramethoxysilane was obtained at the yield of 1% or less based on silicon dioxide. The result is shown in Table 1-3.

Comparative Example 3

Tetramethoxysilane was produced by the same operation as that in Example 1 concerning the reaction condition therein with the exception that 2,2-dimethoxypropane was not added. Tetramethoxysilane was obtained at the yield of 3% based on silicon dioxide. The result is shown in Table 1-3.

Comparative Example 4

Tetramethoxysilane was produced by the same operation as that in Example 1 concerning the reaction condition therein with the exception that carbon dioxide was not introduced. Tetramethoxysilane was obtained at the yield of 3% based on silicon dioxide. The result is shown in Table 1-3.

Comparative Example 5

Tetramethoxysilane was produced by the same operation as that in Example 20 concerning the reaction condition therein with the exception that neither carbon dioxide was introduced, nor 2,2-dimethoxypropane was added. Tetramethoxysilane was obtained at the yield of 1% or less based on silicon dioxide. The result is shown in Table 1-3.

Comparative Example 6

Tetramethoxysilane was produced by the same operation as that in Example 20 concerning the reaction condition therein with the exception that carbon dioxide was not introduced. Tetramethoxysilane was obtained at the yield of 3% based on silicon dioxide. The result is shown in Table 1-3.

Comparative Example 7

Tetramethoxysilane was produced by the same operation as that in Example 23 concerning the reaction condition therein with the exception that 2,2-dimethoxypropane was not added. Tetramethoxysilane was obtained at the yield of 3% based on silicon dioxide. The result is shown in Table 1-3.

TABLE 1-1

|  | Alcohol [g] | Carbon dioxide [MPa] | Metal compound [mol %] | Silicon oxide [g] | Dehydrating agent [g] | Alkali metal compound [g] | Reaction temperature [° c.] | Reaction time [hr] | Yield [%] |
|---|---|---|---|---|---|---|---|---|---|
| Example 1 | 3.0 (MeOH) | 2.0 | — | 0.18 (Q-10) | 5.0 (DMP) | 0.02 (KOH) | 242 | 24 | 47 |
| Example 2 | 3.0 (MeOH) | 2.0 | — | 0.18 (Q-10) | 5.0 (DMP) | 0.02 (KOH) | 242 | 96 | 88 |
| Example 3 | 3.0 (MeOH) | 0.8 | — | 0.18 (Q-10) | 5.0 (DMP) | 0.02 (KOH) | 242 | 24 | 27 |

TABLE 1-1-continued

| | Alcohol [g] | Carbon dioxide [MPa] | Metal compound [mol %] | Silicon oxide [g] | Dehydrating agent [g] | Alkali metal compound [g] | Reaction temperature [° c.] | Reaction time [hr] | Yield [%] |
|---|---|---|---|---|---|---|---|---|---|
| Example 4 | 3.0 (MeOH) | 1.2 | — | 0.18 (Q-10) | 5.0 (DMP) | 0.02 (KOH) | 242 | 24 | 40 |
| Example 5 | 3.0 (MeOH) | 0.4 | — | 0.18 (Q-10) | 5.0 (DMP) | 0.02 (KOH) | 242 | 24 | 7 |
| Example 6 | 3.0 (MeOH) | 3.0 | — | 0.18 (Q-10) | 5.0 (DMP) | 0.02 (KOH) | 242 | 24 | 46 |
| Example 7 | 3.0 (MeOH) | 4.8 | — | 0.18 (Q-10) | 5.0 (DMP) | 0.02 (KOH) | 242 | 24 | 30 |
| Example 8 | 3.0 (MeOH) | 2.0 | — | 0.18 (Q-10) | 5.0 (DMP) | 0.013 (NaOH) | 242 | 24 | 32 |
| Example 9 | 3.0 (MeOH) | 2.0 | — | 0.18 (Q-10) | 5.0 (DMP) | 0.045 (CsOH) | 242 | 24 | 52 |
| Example 10 | 3.0 (MeOH) | 2.0 | — | 0.18 (Q-10) | 5.0 (DMP) | 0.012 (LiOH) | 242 | 24 | 8 |
| Example 11 | 3.0 (MeOH) | 2.0 | — | 0.18 (Q-10) | 5.0 (DMP) | 0.022 ($Li_2CO_3$) | 242 | 24 | 10 |
| Example 12 | 3.0 (MeOH) | 2.0 | — | 0.18 (Q-10) | 5.0 (DMP) | 0.029 ($Na_2CO_3$) | 242 | 24 | 30 |
| Example 13 | 3.0 (MeOH) | 2.0 | — | 0.18 (Q-10) | 5.0 (DMP) | 0.036 ($K_2CO_3$) | 242 | 24 | 56 |
| Example 14 | 3.0 (MeOH) | 2.0 | — | 0.18 (Q-10) | 5.0 (DMP) | 0.069 ($Cs_2CO_3$) | 242 | 24 | 60 |
| Example 15 | 3.0 (MeOH) | 2.0 | — | 0.18 (Q-10) | 5.0 (DMP) | 0.013 (NaF) | 242 | 24 | 17 |

TABLE 1-2

| | Alcohol [g] | Carbon dioxide [MPa] | Metal compound [mol %] | Silicon dioxide [g] | Dehydrating agent [g] | Alkali metal compound [g] | Reaction temperature [° c.] | Reaction Time [hr] | Yield [%] |
|---|---|---|---|---|---|---|---|---|---|
| Example 16 | 3.0 (MeOH) | 2.0 | — | 0.18 (Q-10) | 5.0 (DMP) | 0.018 (KF) | 242 | 24 | 50 |
| Example 17 | 3.0 (MeOH) | 2.0 | — | 0.18 (Q-10) | 5.0 (DMP) | 0.04 (CsF) | 242 | 24 | 53 |
| Example 18 | 3.0 (MeOH) | 0.8 | 1.0 (Ti(OMe)$_4$) | 0.18 (Q-10) | 5.0 (DMP) | 0.02 (KOH) | 242 | 24 | 51 |
| Example 19 | 3.0 (MeOH) | 0.8 | 1.5 (Ti(OMe)$_4$) | 0.18 (Q-10) | 5.0 (DMP) | 0.02 (KOH) | 242 | 24 | 43 |
| Example 20 | 3.0 (MeOH) | 0.8 | 0.1 (Ti(OMe)$_4$) | 0.18 (Q-10) | 5.0 (DMP) | 0.02 (KOH) | 242 | 24 | 33 |
| Example 21 | 3.0 (MeOH) | 0.8 | 0.01 (Ti(OMe)$_4$) | 0.18 (Q-10) | 5.0 (DMP) | 0.02 (KOH) | 242 | 24 | 37 |
| Example 22 | 3.0 (MeOH) | 0.4 | 0.1 (Ti(OMe)$_4$) | 0.18 (Q-10) | 5.0 (DMP) | 0.02 (KOH) | 242 | 24 | 18 |
| Example 23 | 3.0 (MeOH) | 2.0 | 0.1 (Ti(OMe)$_4$) | 0.18 (Q-10) | 5.0 (DMP) | 0.02 (KOH) | 242 | 24 | 48 |
| Example 24 | 3.0 (MeOH) | 2.0 | 0.1 (Zr(OEt)$_4$) | 0.18 (Q-10) | 5.0 (DMP) | 0.02 (KOH) | 242 | 24 | 23 |
| Example 25 | 3.0 (MeOH) | 2.0 | 0.1 (Sn(O$^t$Bu)$_4$) | 0.18 (Q-10) | 5.0 (DMP) | 0.02 (KOH) | 242 | 24 | 29 |
| Example 26 | 3.0 (MeOH) | 2.0 | 0.1 (Nb(OEt)$_5$) | 0.18 (Q-10) | 5.0 (DMP) | 0.02 (KOH) | 242 | 24 | 66 |
| Example 27 | 3.0 (MeOH) | 0.8 | 0.1 (Bu$_2$Sn(OMe)$_2$) | 0.18 (Q-10) | 5.0 (DMP) | 0.02 (KOH) | 242 | 24 | 6 |
| Example 28 | 3.0 (MeOH) | 2.0 | — | 0.18 (Q-10) | 5.0 (DMP) | 0.02 (KOH) | 200 | 24 | 17 |
| Example 29 | 3.0 (MeOH) | 2.0 | — | 0.18 (Q-10) | 5.0 (DMP) | 0.02 (KOH) | 180 | 24 | 6 |
| Example 30 | 3.0 (MeOH) | 2.0 | — | 0.18 (AEROSIL 200) | 5.0 (DMP) | 0.02 (KOH) | 242 | 24 | 48 |

TABLE 1-3

| | Alcohol [g] | Carbon dioxide [MPa] | Metal compound [mol %] | Silicon oxide [g] | Dehydrating agent [g] | Alkali metal compound [g] | Reaction temperature [° c.] | Reaction Time [hr] | Yield [%] |
|---|---|---|---|---|---|---|---|---|---|
| Comparative Example 1 | 3.0 (MeOH) | 2.0 | — | 0.18 (Q-10) | — | — | 242 | 24 | <1 |
| Comparative Example 2 | 3.0 (MeOH) | — | — | 0.18 (Q-10) | — | 0.02 (KOH) | 242 | 24 | <1 |
| Comparative Example 3 | 3.0 (MeOH) | 2.0 | — | 0.18 (Q-10) | — | 0.02 (KOH) | 242 | 24 | 3 |
| Comparative Example 4 | 3.0 (MeOH) | — | — | 0.18 (Q-10) | 5.0 (DMP) | 0.02 (KOH) | 242 | 24 | 3 |
| Comparative Example 5 | 3.0 (MeOH) | — | 0.1 (Ti(OMe)$_4$) | 0.18 (Q-10) | — | 0.02 (KOH) | 242 | 24 | <1 |
| Comparative Example 6 | 3.0 (MeOH) | — | 0.1 (Ti(OMe)$_4$) | 0.18 (Q-10) | 5.0 (DMP) | 0.02 (KOH) | 242 | 24 | 3 |
| Comparative Example 7 | 3.0 (MeOH) | 2.0 | 0.1 (Ti(OMe)$_4$) | 0.18 (Q-10) | — | 0.02 (KOH) | 242 | 24 | 3 |

Q-10: CARiACT Q-10 from FUJI SILYSIA CHEMICAL LTD.

DMP: 2,2-dimethoxypropane

AEROSIL 200: AEROSIL® 200 from NIPPON AEROSIL CO., LTD.

INDUSTRIAL APPLICABILITY

The production method of the present invention enables efficient production of tetraalkoxysilane which is used as a raw material for producing various silane compounds, organic silicone polymer, various silylating agents, colloidal silicas, ceramics, and so on.

The invention claimed is:

1. A method for producing tetraalkoxysilane by using alcohol and silicon oxide, comprising:
a first step of reacting alcohol with carbon dioxide in the presence of a dehydrating agent and/or in a reactor comprising a dehydrating means; and
a second step of reacting a reaction mixture obtained in the first step with silicon oxide,
wherein the alcohol, the silicon oxide, and the carbon dioxide coexist in one reaction system, and thereby the first step and the second step proceed in the one reaction system.

2. The method for producing tetraalkoxysilane according to claim 1, wherein the first step is performed in the presence of at least one metal compound selected from the group consisting of a metal alkoxide, an organic metal oxide, and an inorganic metal oxide.

3. The method for producing tetraalkoxysilane according to claim 2, wherein a metal element of the metal compound is titanium, tin, or zirconium.

4. The method for producing tetraalkoxysilane according to claim 1, wherein the dehydrating agent(s) is (are) an organic dehydrating agent and/or an inorganic dehydrating agent.

5. The method for producing tetraalkoxysilane according to claim 4, wherein the organic dehydrating agent is an acetal represented by the following general formula (1),

(1)

wherein $R^1$ and $R^2$ independently represent a hydrogen atom or a hydrocarbon group of 1 to 15 carbons, and R represents a hydrocarbon group of 1 to 15 carbons, with the proviso that both of $R^1$ and $R^2$ are not a hydrogen atom simultaneously.

6. The method for producing tetraalkoxysilane according to claim 1, wherein the second step is performed in the presence of an alkali metal compound and/or an alkaline earth metal compound.

7. The method for producing tetraalkoxysilane according to claim 6, wherein the alkali metal compound is at least one selected from the group consisting of an alkali metal hydroxide, an alkali metal halide, an alkali metal carbonate, and an alkali metal hydrogen carbonate.

* * * * *